United States Patent
Winslow (10) Patent No.: US 8,052,758 B1
(45) Date of Patent: Nov. 8, 2011

(54) METHOD AND APPARATUS FOR TRIALING A MODULAR HUMERAL HEAD

(75) Inventor: Nathan A Winslow, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 482 days.

(21) Appl. No.: 11/076,293

(22) Filed: Mar. 9, 2005

(51) Int. Cl.
*A61F 2/40* (2006.01)

(52) U.S. Cl. .................................. 623/22.42

(58) Field of Classification Search .... 623/19.11–19.14, 623/22.11–23.38
See application file for complete search history.

(56) References Cited

U.S. PATENT DOCUMENTS

| | | | |
|---|---|---|---|
| 3,815,157 A * | 6/1974 | Skorecki et al. | 623/19.12 |
| 3,869,730 A * | 3/1975 | Skobel | 623/19.12 |
| 3,978,528 A | 9/1976 | Crep | |
| 4,003,095 A | 1/1977 | Gristina | |
| 4,040,131 A | 8/1977 | Gristina | |
| 4,042,980 A * | 8/1977 | Swanson et al. | 623/19.13 |
| 4,135,517 A | 1/1979 | Reale | |
| 4,822,370 A | 4/1989 | Schelhas | |
| 4,865,605 A | 9/1989 | Dines et al. | |
| 4,865,609 A | 9/1989 | Roche | |
| 4,919,670 A | 4/1990 | Dale et al. | |
| 4,957,510 A | 9/1990 | Cremascoli | |
| 4,963,155 A | 10/1990 | Lazzeri et al. | |
| 5,080,685 A | 1/1992 | Bolesky et al. | |
| 5,135,529 A | 8/1992 | Paxson et al. | |
| 5,181,928 A | 1/1993 | Bolesky et al. | |
| 5,201,882 A | 4/1993 | Paxson | |
| 5,222,984 A | 6/1993 | Forte | |
| 5,314,479 A * | 5/1994 | Rockwood et al. | 623/19.14 |
| 5,358,526 A * | 10/1994 | Tornier | 623/19.14 |
| 5,507,817 A | 4/1996 | Craig et al. | |
| 5,507,824 A | 4/1996 | Lennox | |
| 5,549,682 A | 8/1996 | Roy | |
| 5,580,352 A | 12/1996 | Sekel | |
| 5,658,340 A * | 8/1997 | Muller et al. | 623/19.14 |
| 5,702,457 A | 12/1997 | Walch et al. | |
| 5,702,486 A | 12/1997 | Craig et al. | |
| 5,728,161 A | 3/1998 | Camino et al. | |
| 5,902,340 A | 5/1999 | White et al. | |
| 5,910,171 A * | 6/1999 | Kummer et al. | 623/18.11 |
| 5,961,555 A | 10/1999 | Huebner | |
| 6,015,437 A * | 1/2000 | Stossel | 623/19.11 |
| 6,033,439 A | 3/2000 | Camino et al. | |
| 6,102,953 A * | 8/2000 | Huebner | 623/19.11 |

(Continued)

FOREIGN PATENT DOCUMENTS

DE 19509037 C1 9/1996

(Continued)

OTHER PUBLICATIONS

Thabe et al., "Modulares—Vario—Schulter", 6 sheets of pictures.

(Continued)

*Primary Examiner* — David Isabella
*Assistant Examiner* — Ann Schillinger
(74) *Attorney, Agent, or Firm* — Harness, Dickey (57) ABSTRACT

The present invention is directed to a modular shoulder prosthesis measuring device having an adjustable radial offset provided by relative rotation of an adapter interdisposed between the stem and the head. Specifically, the interface configuration between the stem and the adapter, as well as between the adapter and the head are designed such that relative positioning of these components provides a continuous adjustment in the radial offset. Indicia are provided to precisely determine the magnitude and direction of the adjustment being made.

11 Claims, 6 Drawing Sheets

U.S. PATENT DOCUMENTS

| | | | | |
|---|---|---|---|---|
| 6,129,764 | A | * 10/2000 | Servidio | 623/19.11 |
| 6,171,341 | B1 | 1/2001 | Boileau et al. | |
| 6,197,062 | B1 * | 3/2001 | Fenlin | 623/19.12 |
| 6,197,063 | B1 * | 3/2001 | Dews | 623/19.14 |
| 6,206,925 | B1 | 3/2001 | Tornier | |
| 6,228,120 | B1 * | 5/2001 | Leonard et al. | 623/19.12 |
| 6,368,352 | B1 | 4/2002 | Camino et al. | |
| 6,736,852 | B2 | 5/2004 | Callaway et al. | |
| 6,749,637 | B1 * | 6/2004 | Bahler | 623/19.14 |
| 6,942,699 | B2 | 9/2005 | Stone et al. | |
| 2001/0049561 | A1 * | 12/2001 | Dews et al. | 623/19.14 |
| 2002/0016634 | A1 * | 2/2002 | Maroney et al. | 623/19.14 |
| 2003/0028253 | A1 * | 2/2003 | Stone et al. | 623/19.14 |
| 2003/0149485 | A1 * | 8/2003 | Tornier | 623/18.11 |
| 2004/0030394 | A1 * | 2/2004 | Horber | 623/18.11 |
| 2004/0064188 | A1 * | 4/2004 | Ball et al. | 623/19.11 |

FOREIGN PATENT DOCUMENTS

| | | |
|---|---|---|
| EP | 0 257 359 B1 | 3/1988 |
| EP | 0599429 A2 | 6/1994 |
| EP | 0664108 A2 | 7/1995 |
| EP | 0 679 375 A1 | 11/1995 |
| EP | 0 797 964 A1 | 10/1997 |
| EP | 0712617 A1 | 12/1997 |
| FR | 2 574 283 | 6/1986 |
| FR | 2652498 A1 | 4/1991 |
| FR | 2664809 | 1/1992 |
| FR | 2 721 200 | 12/1995 |
| WO | WO 95/22302 | 8/1995 |
| WO | WO 96/17553 | 6/1996 |
| WO | WO 98/46172 | 10/1998 |
| WO | WO 00/15154 | 3/2000 |

OTHER PUBLICATIONS

"Buechel-Pappas™ Total Shoulder System", Endotec, Jul. 1991.

Thabe et al., "Die endoprothetische Versorgung des rheumatischen Schultergelenkes", Aktuelle Rheumatologie, vol. 19 (1994), pp. 155-160 (with English Abstract).

* cited by examiner

METHOD AND APPARATUS FOR TRIALING A MODULAR HUMERAL HEAD

FIELD OF THE INVENTION

The present invention relates to a prosthesis for replacing and reconstructing a portion of the humerus and more specifically to a trialing system for a modular humeral prosthesis which allows for shoulder joint replacement.

BACKGROUND OF THE INVENTION

The present invention relates to a prosthesis for replacing and reconstructing a portion of the humerus and more specifically to a modular humeral prosthesis which allows for shoulder joint replacement.

The shoulder joint is considered to be one of the most complex joints in the body. The scapula, the clavicle and the humerus all meet at the shoulder joint. The head of the humerus fits into a shallow socket of the scapula called the glenoid fossa to form a mobile joint. When the joint is articulated, the humeral head moves in the glenoid fossa to provide a wide range of motion. The shoulder joint may suffer from various maladies including rheumatoid arthritis, osteoarthritis, rotator cuff arthropathy, avascular necrosis, bone fracture or failure of previous joint implants. If severe joint damage occurs and no other means of treatment is found to be effective, then shoulder reconstruction may be necessary.

A shoulder joint prosthesis generally includes the replacement of the ball of the humerus and, optionally, the socket of the shoulder blade with specially designed artificial components. The bio-kinematics, and thus the range of motion in the shoulder vary greatly among prospective patients for reconstruction shoulder surgery. The humeral component typically has a metal shaft or stem with a body portion that is embedded in the resected humerus and a generally hemispherical head portion supported on the stem. The head slidingly engages a glenoid implant on the glenoid fossa. During reconstructive surgery, the components of the prosthesis are matched with the bio-kinematics of the patient in an effort to maintain the natural range of motion of a healthy shoulder joint. Thus, a shoulder prosthesis design must be readily adaptable to a wide range of bio-kinematics for prospective patients.

In this regard, shoulder prostheses are generally available as either unitary structures or modular components. With unitary shoulder prosthesis, a large inventory of differently sized prostheses must be maintained to accommodate the different bone sizes and joint configurations of the prospective patients. With such unitary shoulder prosthesis, the patient is typically evaluated by x-ray to determine the approximate prostheses size needed for reconstruction. A number of differently sized prostheses are selected as possible candidates based upon this preliminary evaluation. Final selection of the appropriately sized prosthesis is made during the surgery. With unitary shoulder prosthesis, each design may represent a compromise that is unable to achieve all of the natural range of motion of a healthy shoulder joint because of the fixed geometric configuration in their design.

Modular prostheses systems which reduce the need to maintain large inventories of various sized components are well known in the art. Conventionally, the humeral prosthesis includes two components—a humeral stem component and a spherical head releasably coupled to the stem. Alternately, a three component design is known in which the stem and shoulder are interconnected with an adapter. In either of the two-piece or three-piece designs, a radial offset or angulator inclination of the head relative to the stem is provided in individual components. Different radial offsets or angular inclinations are achieved through the use of different adapters or heads. In this regard, conventional modular shoulder prosthesis kits include multiple redundant components such as adapters and heads to achieve a range of prosthetic options.

While providing an advantage over the unitary design in reducing the number of components needed, a rather large inventory of head components and/or adapter components must be maintained to provide the desired range of geometric configurations with the conventional modular shoulder prostheses. These components are readily adaptable to provide a range of geometric configurations, i.e. radial offsets of angular inclination while minimizing the number of components required. There is, therefore, a need for a trialing system and method for determining which of these components are needed and their specific orientation.

SUMMARY OF THE INVENTION

In accordance with the teachings of the present invention a modular joint prosthesis system is provided. Specifically, a humeral component for a shoulder prosthesis includes an adapter and a head component which cooperate to provide a range of radial offsets and/or angular inclinations and which are adapted to be used in conjunction with a stem.

In a first embodiment, a measuring instrument for humeral component for a shoulder prosthesis is provided for determining the needed adjustable radial offset of the head with respect to the stem. The present invention includes an adapter interposed between a stem and a head. The adapter is slidably coupled to the head such that relative linear positioning of the adapter on the head will effect a first adjustment in the radial offset. Likewise, the adapter component is rotationally coupled to the stem as such that relative angular position of the adapter will effect a rotational offset adjustment. By selectively positioning the adapter with respect to the head, an infinite adjustment of the radial offset within a given range may be achieved. Indicia are provided at the interface between the adapter and the head to indicate the offset vector (i.e., offset amount and direction).

In a second embodiment, a measuring instrument for a humeral component for a shoulder prosthesis is provided for determining the adjustable radial offset of the head with respect to the stem. The present invention includes an adapter interposed between a stem and a head. The adapter is slidably coupled to a cavity formed in the head such that relative linear positioning of the adapter on the head will effect a first adjustment in the radial offset of the head. Likewise, the adapter component is rotationally coupled to the stem as such that relative angular position of the stem on the adapter will effect a rotational offset adjustment. A fastener is provided to fix the location of the head to the adapter. As presently preferred, indicia are provided on the adapter and the head to indicate the offset vector.

The joint prosthesis measurement system of the present invention provides great flexibility in the adjustment of important bio-kinematic parameters for the prosthesis systems while allowing for the minimizing the number of components required for the modular system. These and other features of the present invention will become apparent from the description and especially taken in conjunction with the accompanying drawings illustrating the invention and the preferred embodiment. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the embodiment(s) is merely exemplary in nature and is in no way intended to limit the invention, its application, or uses.

Figure 1:
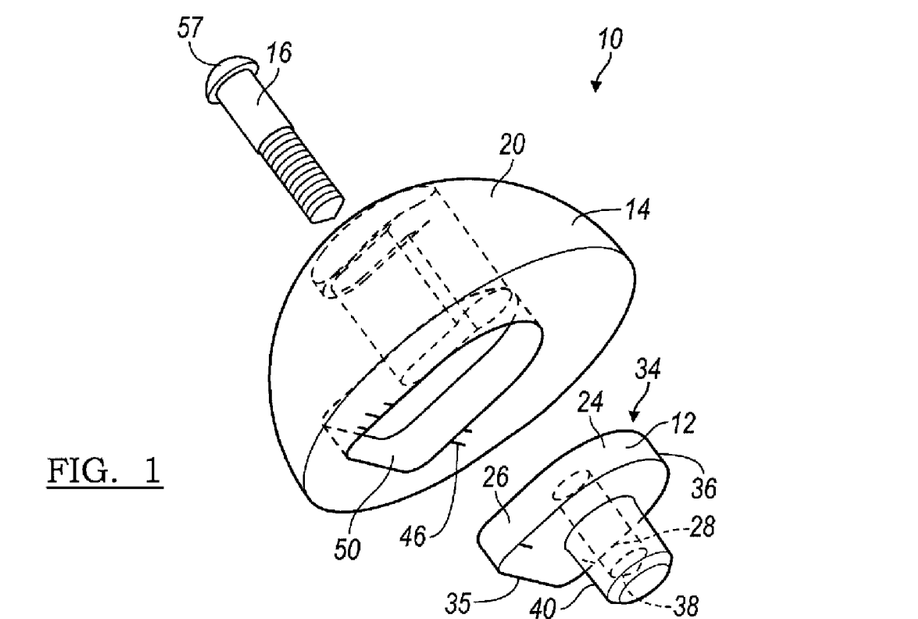
FIG. 1 is an exploded front view of a modular shoulder prosthesis measurement system in accordance with the present invention.

FIG. 1 is an exploded front view of a modular shoulder prosthesis measurement system according to the teachings of the present invention. The measuring device 10 is formed of an adapter 12, a head 14, and a coupling member 16. The adapter 12 is preferably formed of a polymer material, which allow its relative rotation with respect to a fixation member or stem 18. The measuring device 10 is configured to determine both the needed radial offset of an implant head with respect to an implanted fixation member, and also the rotational offset of the head with respect to the fixation member. As further described below, the adapter 12 is slidably coupled to the head 14 such that relative linear positioning of the adapter 12 with the head 14 will affect a first adjustment in the radial offset. Selected positioning of the adapter 12 with respect to the head 14 gives an infinite adjustment of the radial offset within a given range.

Referring generally to FIG. 1, FIGS. 4A-4C and FIG. 6, the adapter 12 has a body portion 24, having a first pair of bearing surfaces 26 and 28. The first pair of bearing surfaces 26 and 28 are slidably coupled to a second pair of bearing surfaces 30 and 32 defined on the head 14. The body portion 24 further has a flat stop surface 34 and a circular stop surface 36 which function to limit the movement of the adapter 12 with respect to the head 14. The adapter 12 further defines a coupling member accepting bore 38 which is optionally threaded. A tapered coupling portion 40 is configured to interface with a Morse taper coupling feature on the stem 18. This tapered coupling portion 40, while shown as a male taper, may optionally be a female taper configured to interface with a male Morse taper formed on the stem 18 or any other connection member.

Figure 2:
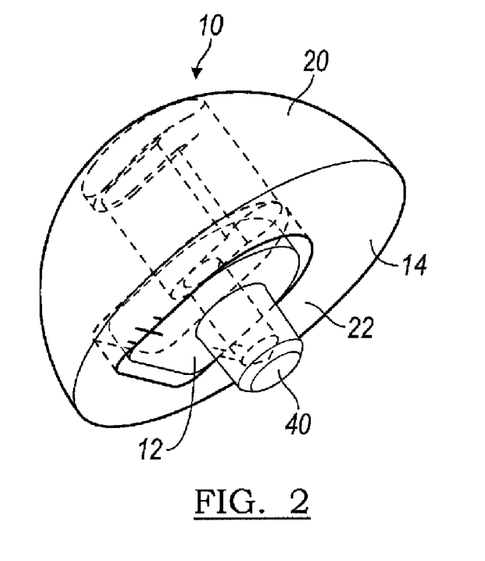
FIG. 2 is a perspective view of the adapter and head components of the device illustrated in FIG. 1 shown in an assembled state.
Figure 3:
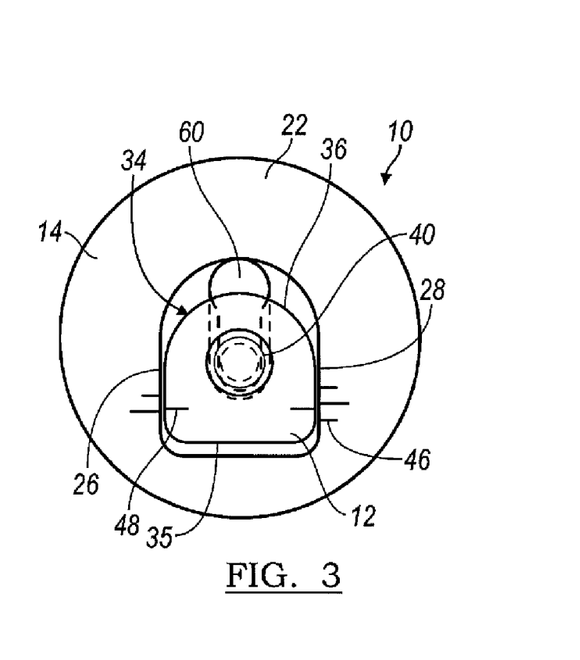
FIG. 3 is a bottom view of the embodiment of the present invention illustrated in FIG. 1.
Figure 4A:
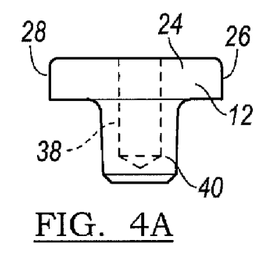
FIGS. 4A-4C are views of the adapter shown in FIG. 1.
Figure 4B:
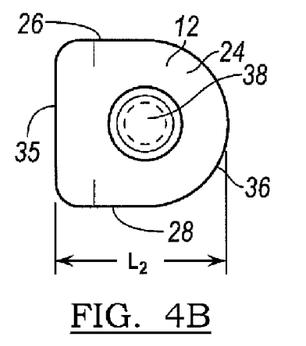
Figure 4C:
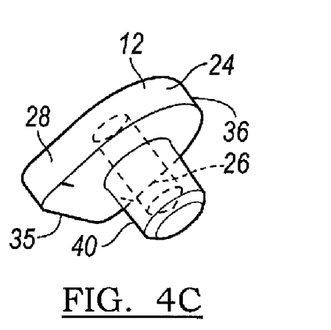
Figure 5A:
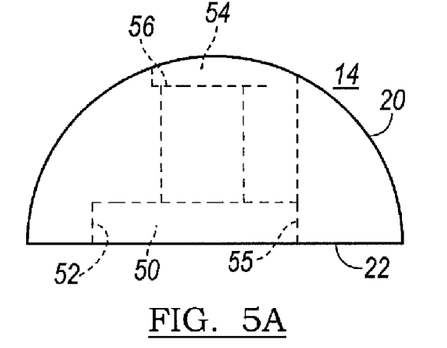
FIGS. 5A-5D are views of the head shown in FIG. 1.
Figure 5B:
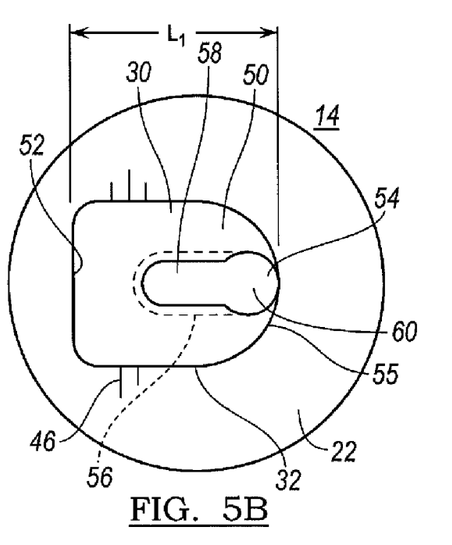
Figure 5C:
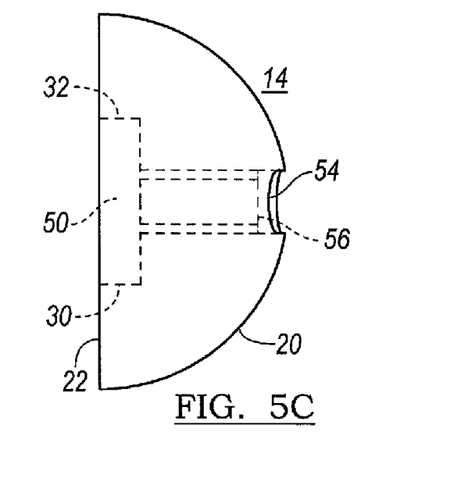
Figure 5D:
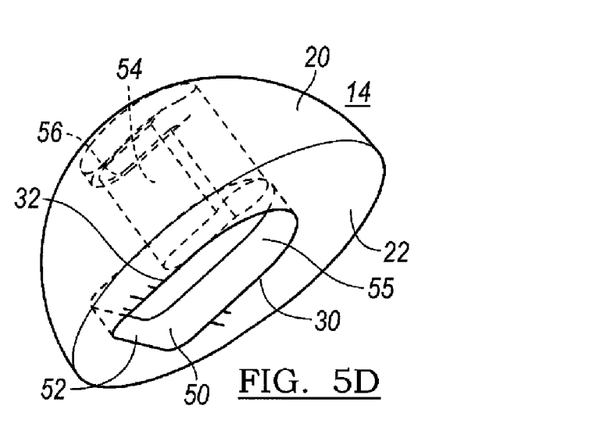

As shown in FIGS. 2 and 3, the bottom surface 34 of the adapter 12 and a bottom surface 22 of the head 14 each have indicia 46 and 48 which indicate the relative positioning of the head 14 with respect to the adapter 12. Additionally, the outer spherical surface 20 has the rotational indicia 43 which is used to determine the relative rotation of the head 14 with respect to the stem 18.

FIGS. 5A-5D represent the head 14 shown in FIG. 1. Defined on the bottom surface 22 is an adapter accepting cavity 50. The cavity 50 has the second pair of bearing surfaces 30 and 32. Additionally, the cavity 50 has flat and curved bearing surfaces 52 and 55 which are configured to interface with the flat and circular bearing surfaces 34 and 36 of the adapter.

The head 14 further defines a through bore 54. The through bore 54 passes through the outer spherical surface 20 and the adapter accepting cavity 50. The through bore 54 has a defined shelf 56 which is configured to support a head portion 57 of the coupling member 16. The through bore 54 further has a slot portion 58 and a circular portion 60 which facilitate transverse movement of the coupling member 16 within the through bore 54. As the cavity 50 has a length $L_1$ which is longer than the length $L_2$ of the adapter 12, the adapter 12 is configured to move transversely within the head 14. The difference in $L_1$ and $L_2$ is the distance of the linear offset of the system. The first pair of bearing surfaces 26 and 28 and second pair of bearing surfaces 30 and 32 are configured so as to prevent relative rotational movement between the adapter 12 and the head 14.

Figure 6:
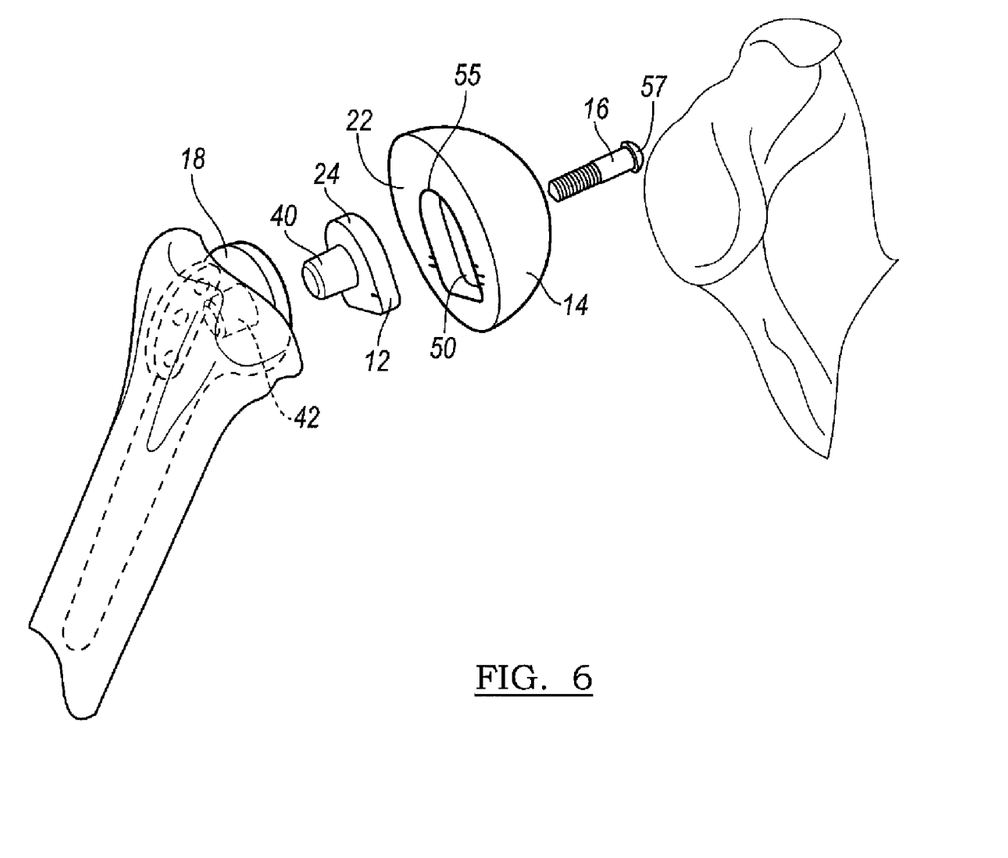
FIG. 6 represents the implantation of the measurement head into a stem component.
Figure 7:
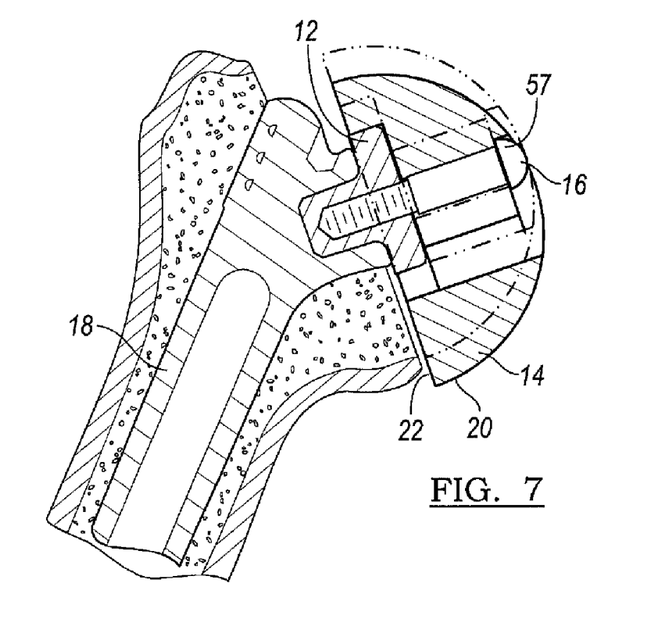
FIG. 7 is cross-sectional view of the trial head coupled to an implanted stem.
Figure 8:
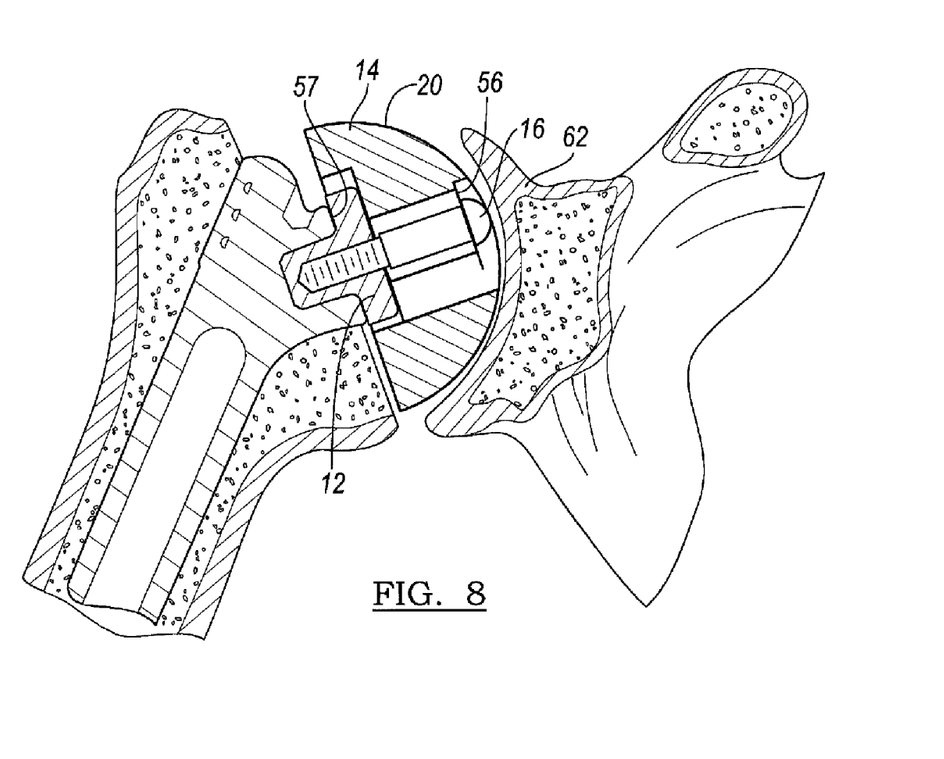
FIG. 8 is cross-sectional view of the trial head coupled to an implanted stem and being positioned into a glenoid.

FIGS. 6-8 show views of the relationship of the measuring device 10 in its environmental surroundings. The taper portion 40 of the adapter 12 is positioned within the taper 42 of the stem 18. Coupling member 16 passes through the bore 54 of the head 14 to loosely couple the head 14 to the adapter 12. After, the head 14 is then positioned against a glenoid 62 which can be natural or an implant, and the kinematic action of the head is then tested.

Figure 9:
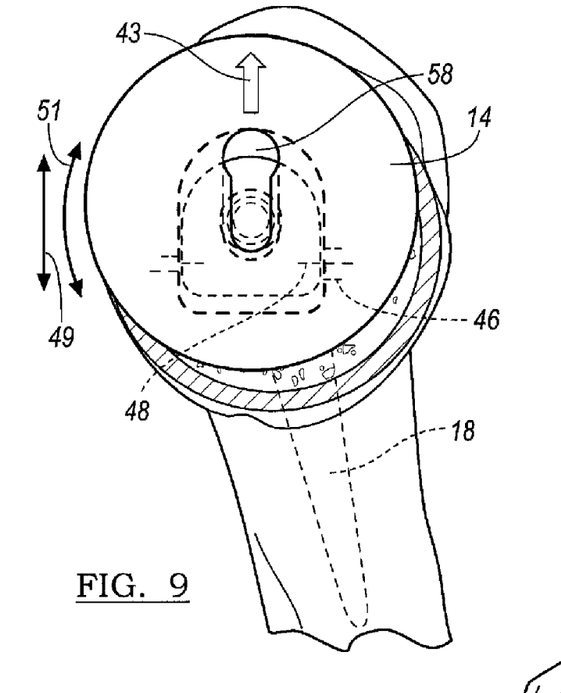
FIGS. 9 and 10 represent the adjustment of the head with respect to the adapter.
Figure 10:
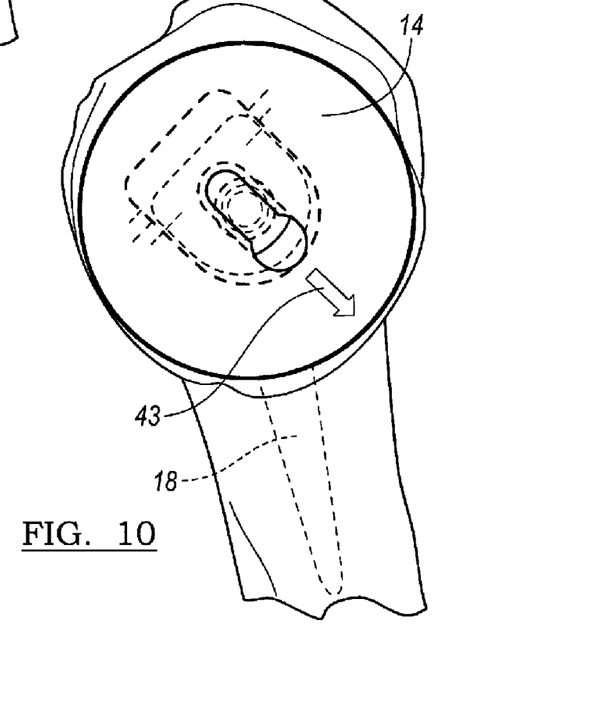
Figure 11:
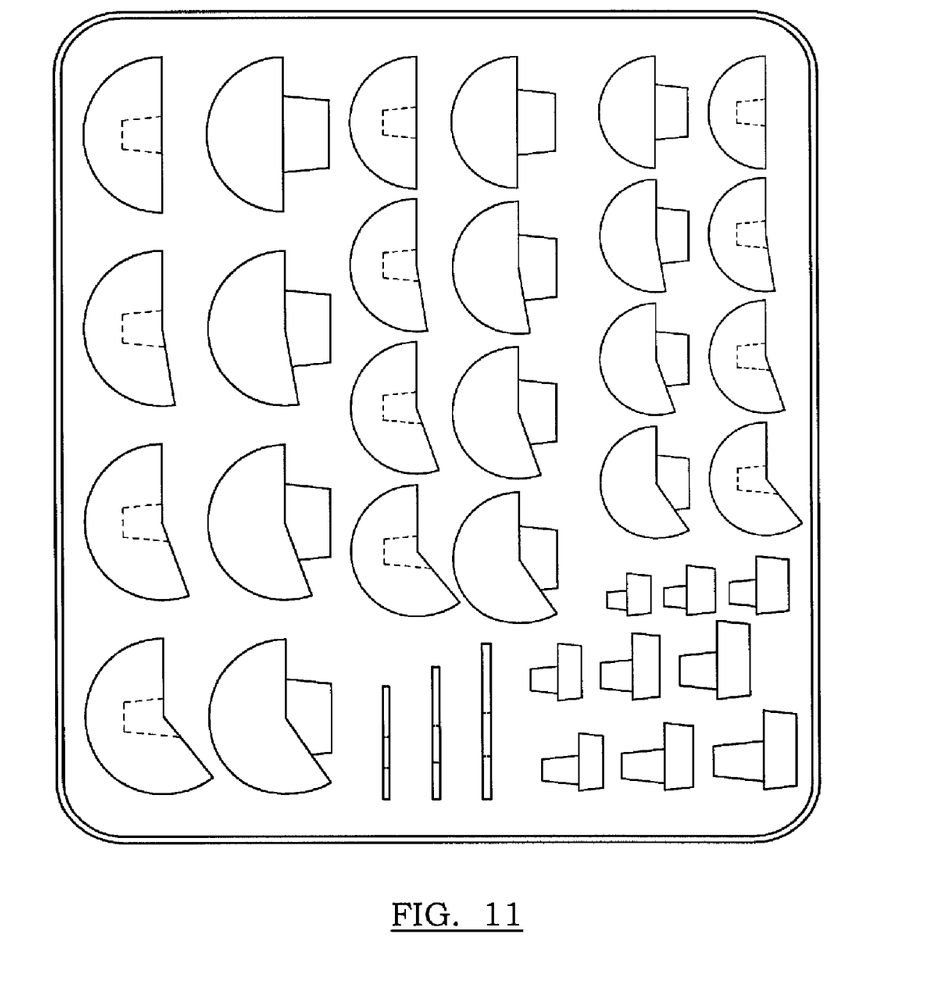
FIG. 11 represents a kit of components.

As seen in FIGS. 8 and 9, should a physician determine that adjustment is necessary, the radial offset 49 of the head 14 can be accomplished by moving it in a first degree of freedom relative to the adapter 12. After this adjustment is made, the physician will then tighten the coupling member 16 to fix the radial position of the head 14 with respect to the adapter 12. The physician can then use the indicia 46 and 48 on the lower stem engaging surface 22 to determine the appropriate implant to use.

As seen in FIG. 9, the adapter 12 and head 14 can be rotated 51 in a second degree of freedom with respect to the stem 18. The rotational indicia 43 on the outer spherical surface 20 can be used to mark the relative location of the implant measuring device 10 with respect to the stem 18. This marking can optionally be made on the biologic tissue surrounding the stem 18. This relative rotation marking is then used by the physician to determine the rotational alignment of the offset implant prior to implantation.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An adjustable trialing prosthesis for use in determining the configuration of a head prosthesis to be coupled to an implanted stem, the adjustable trialing prosthesis comprising:

an adapter including a first pair of generally flat bearing surfaces, said adapter having a cylindrical tapered portion having a taper axis formed thereon; and a head linearly slidably supported by said adapter, wherein said head is positionable relative to said stem through straight translation of said head relative to said adapter for adjusting a linear offset of said head along an angle generally perpendicular to said taper axis thereof, said head defining a second pair of generally planar bearing surfaces slidably engaged with the first pair of generally flat bearing surfaces wherein said head and adapter define a variable sized cavity therebetween when the generally flat bearing surfaces are engaged with the second pair of generally planar bearing surfaces.

2. The adjustable trialing prosthesis of claim 1, wherein said taper is configured to be rotatable relative to the stem when coupled to the stem.

3. The adjustable trialing prosthesis of claim 1, wherein said head portion comprises a rotational indicia.

4. The adjustable trialing prosthesis of claim 1, wherein said head defines an adapter accepting bore.

5. The adjustable trialing prosthesis of claim 4, wherein the adapter accepting bore defines a flat surface which bears against at least one surface of the first pair of flat bearing surfaces.

6. The adjustable trialing prosthesis claim 1, wherein the said first flat bearing surfaces are parallel.

7. The adjustable trialing prosthesis of claim 6, wherein said head defines an adapter accepting bore having a pair of a flat translation surfaces which bear against the pair of flat bearing surfaces.

8. The adjustable trialing prosthesis of claim 1, wherein said head includes a generally hemispherical outer surface adapted for mating engagement with a glenoid cavity of a scapula and a bottom surface having a female taper formed therein.

9. The adjustable trialing prosthesis of claim 1, wherein said adapter includes a plurality of indicia indicating a degree of adjustment of said radial offset.

10. The adjustable trialing prosthesis of claim 1, wherein said head includes an indicia indicating an alignment of said linear offset.

11. The adjustable trialing prosthesis of claim 1 further comprising a fastener which fixes the rotational position of the head with respect to the adapter.

* * * * *

UNITED STATES PATENT AND TRADEMARK OFFICE
CERTIFICATE OF CORRECTION

| | | |
|---|---|---|
| PATENT NO. | : 8,052,758 B1 | Page 1 of 1 |
| APPLICATION NO. | : 11/076293 | |
| DATED | : November 8, 2011 | |
| INVENTOR(S) | : Nathan A. Winslow | |

It is certified that error appears in the above-identified patent and that said Letters Patent is hereby corrected as shown below:

Column 2, line 60, delete "the" after "for"

Column 3, line 23, insert --a-- after "is"

Column 3, line 25, insert --a-- after "is"

Column 4, line 48, delete "51" after "rotated"

Column 6, line 1, insert --of-- after "prosthesis"

Signed and Sealed this
Twenty-fourth Day of July, 2012

David J. Kappos
*Director of the United States Patent and Trademark Office*